(12) United States Patent
Yuan et al.

(10) Patent No.: US 10,106,826 B2
(45) Date of Patent: Oct. 23, 2018

(54) REROUTING THE PHOTORESPIRATION PATHWAY IN PLANTS FOR INCREASING BIOPRODUCT YIELD

(71) Applicant: The Texas A&M University System, College Station, TX (US)

(72) Inventors: Shuhua (Joshua) Yuan, College Station, TX (US); Donald Ort, Urbana, IL (US); Joseph Chappell, Lexington, KY (US); Xinguang Zhu, Urbana, IL (US); Hong Ma, College Station, TX (US); Yong Kyoung Kim, College Station, TX (US)

(73) Assignees: The Texas A&M University System, College Station, TX (US); The University of Illinois at Urbana Champaign, Urbana, IL (US); University of Kentucky, Lexington, KY (US)

( * ) Notice: Subject to any disclaimer, the term of this patent is extended or adjusted under 35 U.S.C. 154(b) by 142 days.

(21) Appl. No.: 14/194,396

(22) Filed: Feb. 28, 2014

(65) Prior Publication Data

US 2014/0283219 A1    Sep. 18, 2014

Related U.S. Application Data

(60) Provisional application No. 61/771,037, filed on Feb. 28, 2013.

(51) Int. Cl.
*C12P 7/62* (2006.01)
*C12P 5/00* (2006.01)
*C12N 15/82* (2006.01)

(52) U.S. Cl.
CPC .......... *C12P 7/625* (2013.01); *C12N 15/8243* (2013.01); *C12P 5/007* (2013.01)

(58) Field of Classification Search
None
See application file for complete search history.

(56) References Cited

U.S. PATENT DOCUMENTS

| | | | | |
|---|---|---|---|---|
| 7,208,318 B2 * | 4/2007 | Hain | ............. | C12N 9/0004 435/320.1 |
| 2011/0023181 A1 * | 1/2011 | Maurino | ............. | C12N 9/0006 800/278 |

OTHER PUBLICATIONS

Millar et al., 2009, The Plant Cell 21: 1625-1631.*
Kebeish et al., 2007, Nature Biotechnology 25: 593-599.*
Devarenne et al., 1998, Archives of Biochemistry and Biophysics 349: 205-215.*
Teli and Timko, 2004, Plant Cell, Tissue and Organ Culture 79: 125-145.*
Busquets et al., 2008, Plant Mol. Biol. 67: 25-36.*
Broun and Somerville, 2001, Proc. Nat. Acad. Sci. USA 98: 8925-8927.*
Wu et al., 2012, Planta 236: 867-877.*
Maier et al., 2012, Frontiers in Plant Science 3(38), doi: 3389/fpls.2012.00038.*
Takahashi et al., "The lost phenotype of chloroplastic photorespiratory bypass in engineered *Arabidopsis*," Poster presentation, The 16th International Congress on Photosynthesis Research, Aug. 12, 2013.
Kebeish et al., "Chloroplastic photorespiratory bypass increases photosynthesis and biomass production in *Arabidopsis thaliana*," *Nat Biotechnol* 25(5):593-9, 2007.
Peterhansel et al., "Photorespiratory bypasses: how can they work?" *J Exper Bot* 64(3):709-15, 2013 (epub 2012).

* cited by examiner

*Primary Examiner* — Amjad Abraham
*Assistant Examiner* — Bratislav Stankovic
(74) *Attorney, Agent, or Firm* — Dentons US LLP

(57) ABSTRACT

The present invention provides methods of producing biological products or increasing production of such products through expression in a plant of a bacterial or plant glycolate catabolic cycle gene, such as glycolate dehydrogenease (GDH), glycolate oxidase (GO), or malate synthase (MS) in combination with a plant gene, such as farnesyl diphosphate synthase (FPS), squalene synthase (SQS), or PLAS. Also provided are plants, plants parts and compositions produced through methods of the present invention. The invention leads to two to five fold increase of end product yield.

10 Claims, 6 Drawing Sheets

REROUTING THE PHOTORESPIRATION PATHWAY IN PLANTS FOR INCREASING BIOPRODUCT YIELD

CROSS REFERENCE TO RELATED APPLICATIONS

This application claims the benefit of U.S. Provisional Application No. 61/771,037, filed Feb. 28, 2013, herein incorporated by reference in its entirety.

FIELD OF THE INVENTION

The present invention relates to the field of plant molecular biology and plant genetic engineering. More specifically, the present invention relates to methods for modifying photorespiration in plants and the synergistic production of bioproducts.

BACKGROUND OF THE INVENTION

Photorespiration may be initiated by ribulose-1,5-bisphosphate carboxylase oxygenase (RuBisCo) binding with $O_2$ to produce 2-phosphoglycolate, or by RuBisCo binding with $CO_2$ to produce 3-phosphoglycerate. These two reactions, catalyzed by the same enzyme, are diametrically opposed to each other, thus making photorespiration a very expensive process metabolically. It is estimated that 25% of the carbon fixed by plants during photosynthesis is lost in the process of photorespiration.

SUMMARY OF THE INVENTION

The present invention provides a method of producing a biological product in a plant, comprising expressing in the plant a bacterial gene selected from the group consisting of glycolate dehydrogenase (GDH), glycolate oxidase (GO), and malate synthase (MS), in combination with a plant gene selected from the group consisting of TPS, squalene synthase (SQS), farnesyl pyrophosphate synthase (FPPS), which is also known as farnesyl diphosphate synthase (FPS), and poly lactic acid (PLA) synthase (PLAS). In certain embodiments, a biological product is produced by the method of the present invention, or the production of a biological product is increased. In embodiments, the plant may be a monocotyledonous plant such as *Oryza, Arundo, Hordeum*, or *Triticum*, or a dicotyledonous plant such as *Arabidopsis, Nicotiana, Lycopersicon, Glycine, Brassica, Vitis, Solanum, Manihot, Arachis, Malus, Citrus, Gossypium, Lactuca*, or *Raphanus*. In another embodiment, expression of the bacterial gene in the plant produces an elevated level of said biological product. In other embodiments, the biological product may be a biofuel or a biofuel intermediate, a therapeutic compound such as a nutraceutical compound or a terpenoid-derived compound, a terpene compound with other applications, a bioplastic such as one selected from the group consisting of PHA, PHB, and PLA, a terpene, or a carbon-containing product. In still further embodiments, the plant gene may be over-expressed, or the bacterial and plant genes may be expressed together.

In another aspect, the present invention provides a method of producing a biological product from a plant or an alga, comprising coupling a carbon-concentrating mechanism and optimization of an end product pathway. In embodiments, the biological product may be a biofuel or a therapeutic compound.

BRIEF DESCRIPTION OF THE FIGURES

FIG. 2(A) shows the increase of flux to a terpene product resulting from photorespiratory bypass as shown in FIG. 1. FIG. 2(B) shows that the increase of flux to a terpene product will not decrease the photosynthesis rate as fast as the increase in terpene yield, according to the pathway design of GDHD, GDHE, GDHF, and MS. FIG. 2(C) shows the same result as above according to the pathway with GO, MS, and CAT.

DETAILED DESCRIPTION OF THE INVENTION

Figure 1:
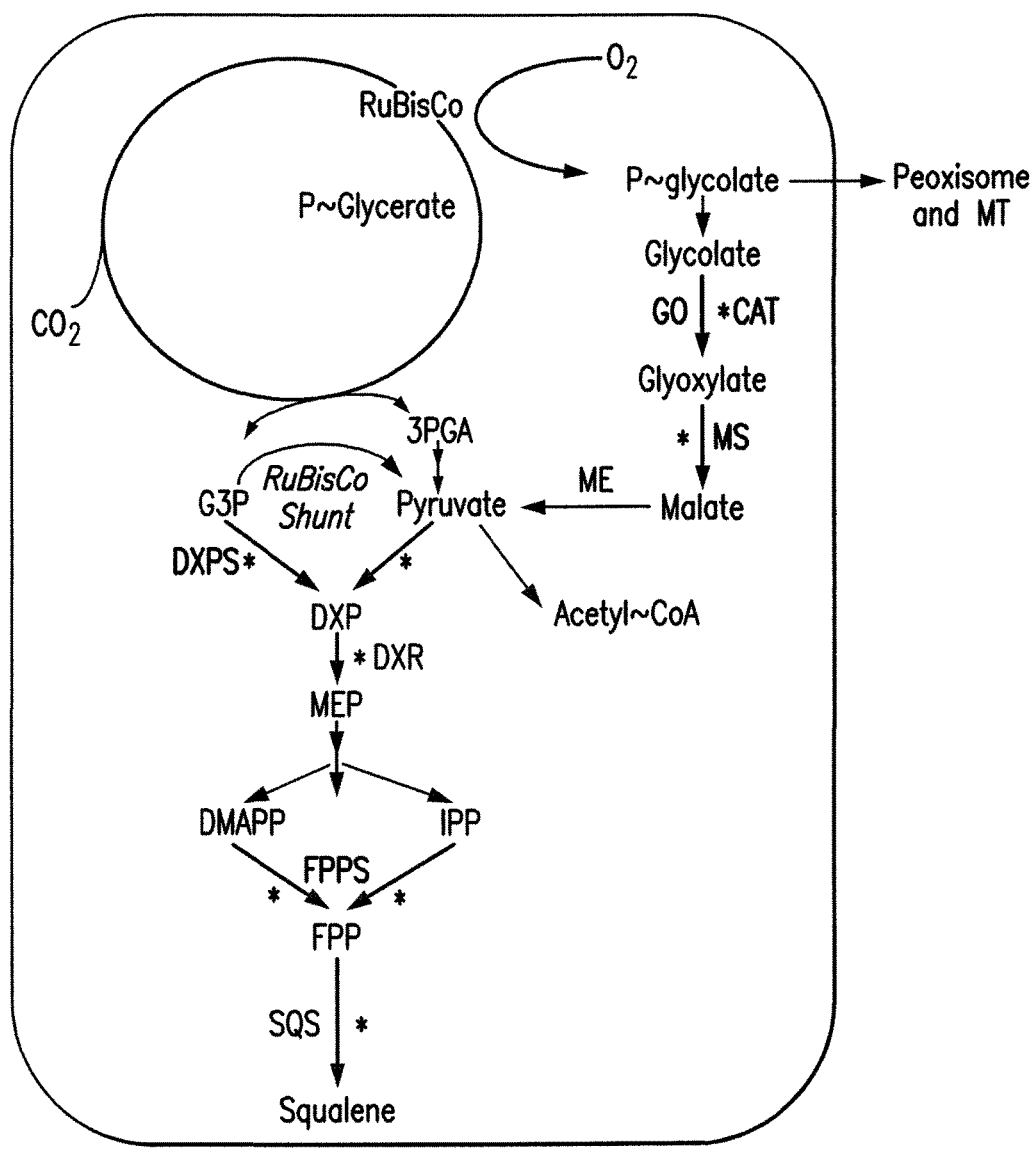
FIG. 1—shows a rerouting pathway design. The top area represents Pathway I. The middle area represents Pathway II. The bottom area represents the terpenoid biosynthesis pathway. *Indicates enzymes that may be modified.

The present invention provides a method for rechanneling the products of photorespiration to increase production of valuable compounds via engineering of the photorespiration pathway. Embodiments of the present invention provide various approaches for engineering photorespiration.

In one embodiment, a gene from a bacterial glycolate catabolic cycle may be introduced into the plant to result in photorespiration bypass. Enzymes of the glycolate catabolic cycle that may be useful in the present invention include, but are not limited to, glycolate dehydrogenase (GDH), glycolate oxidase (GO), malate synthase (MS), or catalase (CAT). In another embodiment of the invention, photorespiration and photosynthesis bypass may be coupled with end product production (i.e. terpene biosynthesis or polymer biosynthesis). Such a coupling process may be performed by genetic engineering of a plant to comprise or couple a gene or multiple genes from a carbon concentrating pathway or a biosynthetic pathway, such as photorespiration product cycling, photosynthesis, terpene biosynthesis, and/or polymer biosynthesis. For example, photorespiration rechanneling or bypass in a plant through expression of a gene from a bacterial glycolate catabolic cycle may be coupled with downstream terpene synthesis through overexpression of, for example, FPPS, SQS, PLAS, or LMS, in the plant terpene synthesis pathway. Thus, the present invention provides a strategy to channel the photorespiration product 2-phosphoglycerate (glycolate) both back to the Calvin cycle and to use it to leverage higher yield of bioproducts including, but not limited to, squalene, astaxanthin, leutin, other terpenoids, lipids, polyhydroxyalkanoate (PHA) Poly-β-hydroxybutyrate (PHB), poly(lactic acid) or polylactide (PLA), and others.

In another embodiment, the coupling of photorespiration bypass and production of a bioproduct as described above may be further coupled to the 2-C-methyl-D-erythritol 4-phosphate (MEP) pathway. In an embodiment, such a further coupling may comprise coupling to a bacterial gene from the MEP pathway, including 1-deoxy-d-xylulose 5-phosphate synthase (DXPS) and 1-deoxy-d-xylulose 5-phosphate reductase (DXR), for channeling carbon to the MEP pathway to enhance terpene production in a plant.

Despite previous findings, photorespiration re-routing has not been used for purposes other than growth improvement. Additionally, such findings relating to plant growth by photorespiration bypass have proven difficult to repeat. The present invention thus represents an improvement over the art by providing a method of producing a bioproduct in a plant by introducing into a plant a bacterial gene that will break down the products of photorespiration and enable the plant to produce greater amounts of the bioproduct.

By rechanelling the products of photorespiration, the production of increased amounts of bioproducts may be possible. For example, concentrating $CO_2$ in the chloroplast may increase the photosynthetic efficiency and carbon fixation of the plant and thus provide more precursors for these bioproducts. In addition, directly channelling additional carbons to the relevant biosynthesis pathways may also allow production of increased bioproducts. The effect is referred to as carbon repartitioning, in which carbon that would otherwise go to photorespiration will be repartitioned to produce terpene and other bioproducts. Further, reducing the amount of energy needed for recycling of C2 products in mitochondria and peroxisomes may further synergize the production of bioproducts in a plant.

The present invention represents a straightforward yet powerful solution to enable economically viable plant bioproduct production. The approach also has the potential to enhance the production of a variety of plant bioproducts, such as terpenes (including squalene, leutin, astaxanthin, and others), PHA, PHB, PLA, lipids, and others. The present invention dramatically decreases the bioproduct production costs for plants and can assist in the production of economically viable biofuel, pharmaceuticals, and chemicals. The present invention also provides a solution to increase the photosynthesis efficiency and biomass of C3 plants.

The term "bioproduct" as used herein refers to a product produced as a result of a biological process, such as photosynthesis or photorespiration, or from a biological material, such as a plant or a plant part. Many bioproducts have important commercial value. For example, β-caryophyllene, a major component of *Copaifera* oleoresin, can be directly used as a diesel fuel. In addition, Artemisinin is an antimalarial drug isolated from *Artemisia annua* L. Squalene recently has been shown to be an important nutraceutical and can be widely used as a vaccine carrier. Carotenoids such as lycopene, β-carotene, and astaxanthin are used as food colorants, animal feed supplements, and for nutritional and cosmetic purposes. More recently, carotenoids have received attention for their significant antioxidant activities and for their roles in inhibiting the onset of chronic diseases. PHA, PHB, and PLA are promising bioplastics. Supply of these useful compounds from natural sources is limiting and expensive, and the cost of their total synthesis is prohibitive, and thus novel methods for their production are needed.

Terpenes, also referred to as terpenoids, are the largest group of natural products. All terpenoids are synthesized from a five-carbon precursor, isopentenyl diphosphate (IPP). Based on the isoprene structure and the length of the carbon chain, terpenoids can be classified into monoterpenes (10-carbon), sesquiterpenes (15-carbon), diterpenes (20-carbon), triterpenes (30-carbon) and tetraterpenes (40-carbon). In higher plants, terpenoids are synthesized with either the chloroplastic non-mevalonate (MEP) pathway, or the cytosolic mevalonate (MEV) pathway.

DNA Molecules

As used herein, the term "DNA" or "DNA molecule" refers to a double-stranded DNA molecule of genomic or synthetic origin, i.e. a polymer of deoxyribonucleotide bases or a polynucleotide molecule, read from the 5' (upstream) end to the 3' (downstream) end. As used herein, the term "DNA sequence" refers to the nucleotide sequence of a DNA molecule. The nomenclature used herein corresponds to that of Title 37 of the United States Code of Federal Regulations §1.822, and set forth in the tables in WIPO Standard ST.25 (1998), Appendix 2, Tables 1 and 3.

As used herein, the term "isolated DNA molecule" refers to a DNA molecule at least partially separated from other molecules normally associated with it in its native or natural state. In one embodiment, the term "isolated" refers to a DNA molecule that is at least partially separated from some of the nucleic acids that normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state.

Any number of methods well known to those skilled in the art can be used to isolate and manipulate a DNA molecule, or fragment thereof, as disclosed in the present invention. For example, polymerase chain reaction (PCR) technology can be used to amplify a particular starting DNA molecule and/or to produce variants of the original molecule. DNA molecules, or fragment thereof, can also be obtained by other techniques, such as by directly synthesizing the fragment by chemical means, as is commonly practiced by using an automated oligonucleotide synthesizer.

Regulatory Elements

A regulatory element is a DNA molecule having gene regulatory activity, i.e. one that has the ability to affect the transcription and/or translation of an operably linked transcribable polynucleotide molecule. Regulatory elements in accordance with the present invention may be any regulatory element useful for bypass and terpene design. The term "gene regulatory activity" thus refers to the ability to affect the expression pattern of an operably linked transcribable polynucleotide molecule by affecting the transcription and/or translation of that operably linked transcribable polynucleotide molecule. As used herein, a transcriptional regulatory expression element group may be comprised of expression elements, such as enhancers, promoters, leaders, and introns, operably linked. Thus, a transcriptional regulatory expression element group may be comprised, for instance, of a promoter operably linked 5' to a leader sequence, which is in turn operably linked 5' to an intron sequence. The intron sequence may be comprised of a sequence beginning at the point of the first intron/exon splice junction of the native sequence and may be further comprised of a small leader fragment comprising the second intron/exon splice junction so as to provide for proper intron/exon processing to facilitate transcription and proper processing of the resulting transcript. Leaders and introns may positively affect transcription of an operably linked transcribable polynucleotide molecule, as well as translation of the resulting transcribed RNA. The pre-processed RNA molecule comprises leaders and introns, which may affect the post-transcriptional processing of the transcribed RNA and/or the export of the transcribed RNA molecule from the cell nucleus into the cytoplasm. Following post-transcriptional processing of the transcribed RNA molecule, the leader sequence may be retained as part of the final messenger RNA and may positively affect the translation of the messenger RNA molecule.

Regulatory elements such as promoters, leaders, introns, and transcription termination regions are DNA molecules that have gene regulatory activity and play an integral part in the overall expression of genes in living cells. Isolated regulatory elements, such as promoters and leaders, that function in plants are therefore useful for modifying plant phenotypes through the methods of genetic engineering.

Regulatory elements may be characterized by their expression pattern effects (qualitatively and/or quantitatively), e.g. positive or negative effects and/or constitutive or other effects, such as by their temporal, spatial, developmental, tissue, environmental, physiological, pathological, cell cycle, and/or chemically responsive expression pattern, and any combination thereof, as well as by quantitative or qualitative indications. A promoter may be useful as a regulatory element for modulating the expression of an operably linked transcribable polynucleotide molecule.

As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as an mRNA, a dsRNA, a tRNA, an rRNA, a miRNA, and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, i.e. a promoter produced through the fusion of two or more heterologous DNA molecules. In specific embodiments of the invention, such molecules and any variants or derivatives thereof as described herein are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" that provides a basal level of transcription and is comprised of a TATA box or equivalent sequence for recognition and binding of the RNA polymerase II complex for initiation of transcription.

Compositions derived from a promoter useful for the present invention, such as internal or 5' deletions, for example, can be produced using methods known in the art to improve or alter expression, including by removing elements that have either positive or negative effects on expression; duplicating elements that have positive or negative effects on expression; and/or duplicating or removing elements that have tissue- or cell-specific effects on expression. Further deletions can be made to remove any elements that have positive or negative; tissue specific; cell specific; or timing specific (such as, but not limited to, circadian rhythms) effects on expression. The efficacy of the modifications, duplications or deletions described herein on the desired expression aspects of a particular transgene may be tested empirically in stable and transient plant assays, such as those described in the working examples herein, so as to validate the results, which may vary depending upon the changes made and the goal of the change in the starting molecule.

As used herein, the term "leader" refers to a DNA molecule isolated from the untranslated 5' region (5' UTR) of a genomic copy of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable polynucleotide molecule. Leader molecules may be used with a heterologous promoter or with their native promoter. Promoter molecules of the present invention may thus be operably linked to their native leader or may be operably linked to a heterologous leader. In specific embodiments, such sequences may be provided defined as being capable of acting as a leader in a host cell, including, for example, a transgenic plant cell. In one embodiment, such sequences are decoded as comprising leader activity.

A leader sequence (5' UTR) in accordance with the present invention may be comprised of regulatory elements or may adopt secondary structures that can have an effect on transcription or translation of a transgene. Such a leader sequence may be used in accordance with the present invention to make chimeric regulatory elements that affect transcription or translation of a transgene. In addition, such a leader sequence may be used to make chimeric leader sequences that affect transcription or translation of a transgene.

The introduction of a foreign gene into a new plant host does not always result in high expression of the incoming gene. Furthermore, if dealing with complex traits, it is sometimes necessary to modulate several genes with spatially or temporally different expression patterns. Introns can principally provide such modulation. However, multiple uses of the same intron in one plant has been shown to exhibit disadvantages. In those cases, it is necessary to have a collection of basic control elements for the construction of appropriate recombinant DNA elements. The number of introns known in the art to have expression-enhancing properties is limited, and thus, alternatives are needed.

In accordance with the present invention, a promoter or promoter fragment may be analyzed for the presence of known promoter elements, i.e. DNA sequence characteristics, such as a TATA-box and other known transcription factor binding site motifs. Identification of such known promoter elements may be used by one of skill in the art to design variants of a promoter having a similar expression pattern to the original promoter.

As used herein, the term "enhancer" or "enhancer element" refers to a cis-acting transcriptional regulatory element (a cis-element), which confers an aspect of the overall expression pattern, but is usually insufficient alone to drive transcription of an operably linked polynucleotide sequence. Unlike promoters, enhancer elements do not usually include a transcription start site (TSS), or TATA box or equivalent sequence. A promoter may naturally comprise one or more enhancer elements that affect the transcription of an operably linked polynucleotide sequence. An isolated enhancer element may also be fused to a promoter to produce a chimeric promoter cis-element, which confers an aspect of the overall modulation of gene expression. A promoter or promoter fragment may comprise one or more enhancer elements that affect the transcription of operably linked genes. Many promoter enhancer elements are believed to bind DNA-binding proteins and/or affect DNA topology, producing local conformations that selectively allow or restrict access of RNA polymerase to the DNA template, or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e. deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST®. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present invention.

In plants, the inclusion of some introns in gene constructs leads to increased mRNA and protein accumulation relative to constructs lacking the intron. This effect has been termed "intron mediated enhancement" (IME) of gene expression (Mascarenhas et al., (1990) *Plant Mol. Biol.* 15:913-920). Introns known to stimulate expression in plants have been identified in maize genes [e.g., tubA1, Adh1, Sh1, Ubi1 (Jeon et al., *Plant Physiol.* 123:1005-1014, 2000; Callis et al., *Genes Dev.* 1:1183-1200, 1987; Vasil et al., *Plant Physiol.* 91:1575-1579, 1989; Christiansen et al., *Plant Mol. Biol.* 18:675-689, 1992) and in rice genes (e.g., salt, tpi: McElroy et al., *Plant Cell* 2:163-171, 1990; Xu et al., *Plant Physiol.* 106:459-467, 1994). Similarly, introns from dicotyledonous plant genes such as petunia (e.g., rbcS), potato (e.g., st-ls1) and *Arabidopsis thaliana* (e.g., ubq3 and pat1) have been found to elevate gene expression rates (Dean et al., *Plant Cell* 1:201-208, 1989; Leon et al., *Plant Physiol.* 95:968-972, 1991; Norris et al., *Plant Mol. Biol.* 21:895-906, 1993; Rose and Last, *Plant J.* 11:455-464, 1997). It has been shown that deletions or mutations within the splice sites of an intron reduce gene expression, indicating that splicing might be needed for IME (Mascarenhas et al., *Plant Mol. Biol.* 15:913-920, 1990; Clancy and Hannah, *Plant Physiol.* 130:918-929, 2002). However, such splicing is not required for a certain IME in dicotyledonous plants, as shown by point mutations within the splice sites of the pat1 gene from *A. thaliana* (Rose and Beliakoff, *Plant Physiol.* 122:535-542, 2000).

Enhancement of gene expression by introns is not a general phenomenon because some intron insertions into recombinant expression cassettes fail to enhance expression (e.g., introns from dicot genes such as the rbcS gene from pea, the phaseolin gene from bean, and the stls-1 gene from *Solanum tuberosum*) and introns from maize genes (the ninth intron of the adh1 gene, and the first intron of the hsp81 gene) (Chee et al., *Gene* 41:47-57, 1986; Kuhlemeier et al., *Mol Gen Genet.* 212:405-411, 1988; Mascarenhas et al., *Plant Mol. Biol.* 15:913-920, 1990; Sinibaldi and Mettler, In W E Cohn, K Moldave, eds, Progress in Nucleic Acid Research and Molecular Biology, Vol 42. Academic Press, New York, pp 229-257, 1992; Vancanneyt et al., *Mol. Gen. Genet.* 220:245-250, 1990). Therefore, not every intron can be employed to manipulate the gene expression level of non-endogenous genes or endogenous genes in transgenic plants. What characteristics or specific sequence features must be present in an intron sequence in order to enhance the expression rate of a given gene is not known in the art, and therefore it is not possible to predict whether a given plant intron, when used heterologously, will cause IME.

As used herein, the term "chimeric" refers to a single DNA molecule produced by fusing a first DNA molecule to a second DNA molecule, where neither the first nor the second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments, for example the fusion of a promoter to an enhancer element. Thus, the design, construction, and use of chimeric promoters according to the methods disclosed herein for modulating the expression of operably linked transcribable polynucleotide molecules are encompassed by the present invention.

As used herein, the term "variant" refers to a second DNA molecule that is similar in composition, but not identical to, a first DNA molecule, and yet the second DNA molecule still maintains the general functionality, i.e. same or similar expression pattern, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. A "variant" may also encompass a regulatory element having a nucleotide sequence comprising a substitution, deletion, and/or insertion of one or more nucleotides of a reference sequence, wherein the derivative regulatory element has more or less or equivalent transcriptional or translational activity than the corresponding parent regulatory molecule. The regulatory element "variants" will also encompass variants arising from mutations that naturally occur in bacterial and plant cell transformation. In the present invention, a polynucleotide sequence may be used to create variants that are similar in composition, but not identical to, the polynucleotide sequence of the original regulatory element, while still maintaining the general functionality, i.e. same or similar expression pattern, of the original regulatory element. Production of such variants of the present invention is well within the ordinary skill of the art in light of the disclosure and is encompassed within the scope of the present invention. Chimeric regulatory element "variants" comprise the same constituent elements as a reference sequence, but the constituent elements comprising the chimeric regulatory element may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting chimeric regulatory element "variant" can be comprised of the same, or variants of the same, constituent elements of the reference sequence but differ in the sequence or sequences that comprise the linking sequence or sequences which allow the constituent parts to be operatively linked.

Constructs

As used herein, the term "construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule, where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell. A vector according to the present invention may include an expression cassette or transgene cassette isolated from any of the aforementioned molecules.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. A leader, for example, is operably linked to coding sequence when it is capable of serving as a leader for the polypeptide encoded by the coding sequence.

Constructs of the present invention may be provided, in one embodiment, as double Ti plasmid border DNA constructs that have right border (RB or AGRtu.RB) and left border (LB or AGRtu.LB) regions of the Ti plasmid isolated from *Agrobacterium tumefaciens* comprising a T-DNA, that along with transfer molecules provided by the *A. tumefaciens* cells that permit the integration of the T-DNA into the genome of a plant cell (see, for example, U.S. Pat. No. 6,603,061). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes a Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* AB1, C58, or LBA4404; however, other strains known to those skilled in the art of plant transformation can function in the present invention.

Methods are known in the art for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells are well known to one skilled in the art (see, for example, Molecular Cloning: A Laboratory Manual, 3rd edition Volumes 1, 2, and 3, J. Sambrook, D. W. Russell, and N. Irwin, Cold Spring Harbor Laboratory Press, 2000). Methods for making recombinant vectors particularly suited to plant transformation include, without limitation, those described in U.S. Pat. Nos. 4,971, 908; 4,940,835; 4,769,061; and 4,757,011 in their entirety. These types of vectors have also been reviewed in the scientific literature (see, for example, Rodriguez, et al., Vectors: A Survey of Molecular Cloning Vectors and Their Uses, Butterworths, Boston, 1988; and Glick et al., Methods in Plant Molecular Biology and Biotechnology, CRC Press, Boca Raton, Fla., 1993). Typical vectors useful for expression of nucleic acids in higher plants are well known in the art and include vectors derived from the tumor-inducing (Ti) plasmid of *A. tumefaciens* (Rogers et al., *Methods in Enzymology* 153: 253-277, 1987). Other recombinant vectors useful for plant transformation, including the pCaMVCN transfer control vector, have also been described in the scientific literature (see, for example, Fromm et al., *Proc. Natl. Acad. Sci. USA* 82: 5824-5828, 1985).

Various regulatory elements may be included in a construct, including any of those provided herein. Any such regulatory elements may be provided in combination with other regulatory elements. Such combinations can be designed or modified to produce desirable regulatory features. In one embodiment, constructs of the present invention comprise at least one regulatory element operably linked to a transcribable polynucleotide molecule operably linked to a 3' transcription termination molecule.

Constructs of the present invention may include any promoter or leader provided herein or known in the art. For example, a promoter of the present invention may be operably linked to a heterologous non-translated 5' leader such as one derived from a heat shock protein gene (see, for example, U.S. Pat. Nos. 5,659,122 and 5,362,865). Alternatively, a leader of the present invention may be operably linked to a heterologous promoter such as the Cauliflower Mosaic Virus (CaMV) 35S transcript promoter (see, for example, U.S. Pat. No. 5,352,605).

As used herein, the term "intron" refers to a DNA molecule that may be isolated or identified from the genomic copy of a gene and may be defined generally as a region spliced out during mRNA processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable polynucleotide molecule. A DNA construct may comprise an intron, and the intron may or may not be heterologous with respect to the transcribable polynucleotide molecule sequence. Examples of introns in the art include the rice actin intron (U.S. Pat. No. 5,641,876) and the corn HSP70 intron (U.S. Pat. No. 5,859,347). Further, when modifying intron/exon boundary sequences, it may be preferable to avoid using the nucleotide sequence AT or the nucleotide A just prior to the 5' end of the splice site (GT) and the nucleotide G or the nucleotide sequence TG, respectively, immediately after 3' end of the splice site (AG) to eliminate the potential of unwanted start codons formed during processing of the messenger RNA into the final transcript. The sequence around the 5' or 3' end splice junction sites of the intron can thus be modified in this manner.

As used herein, the term "3' transcription termination molecule" or "3' UTR" refers to a DNA molecule that is used during transcription to produce the 3' untranslated region (3' UTR) of an mRNA molecule. The 3' untranslated region of an mRNA molecule may be generated by specific cleavage and 3' polyadenylation (polyA tail). A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region (see, Fraley, et al., *Proc. Natl. Acad. Sci. USA*, 80: 4803-4807, 1983); wheat hsp17 3' region; pea rubisco small subunit 3' region; cotton E6 3' region (U.S. Pat. No. 6,096,950); 3' regions disclosed in WO/0011200 A2; and the coixin 3' UTR (U.S. Pat. No. 6,635,806).

3' UTRs typically find beneficial use for the recombinant expression of specific genes. In animal systems, machinery of 3' UTRs has been well defined (e.g., Zhao et al., *Microbiol Mol Biol Rev* 63:405-445, 1999; Proudfoot, *Nature* 322:562-565, 1986; Kim et al., *Biotechnology Progress* 19:1620-1622, 2003; Yonaha and Proudfoot, *EMBO J.* 19:3770-3777, 2000; Cramer et al., *FEBS Letters* 498:179-182, 2001; Kuerstem and Goodwin, *Nature Reviews Genetics* 4:626-637, 2003). Effective termination of RNA transcription is required to prevent unwanted transcription of trait-unrelated (downstream) sequences, which may interfere with trait performance. Arrangement of multiple gene expression cassettes in local proximity to one another (e.g. within one T-DNA) may cause suppression of gene expression of one or more genes in said construct in comparison to independent insertions (Padidam and Cao, *BioTechniques* 31:328-334, 2001). This may interfere with achieving adequate levels of expression, for instance in cases where strong gene expression from all cassettes is desired.

In plants, clearly defined polyadenylation signal sequences are not known. Hasegawa et al. (*Plant J.* 33:1063-1072, 2003) were not able to identify conserved polyadenylation signal sequences in both in vitro and in vivo systems in *Nicotiana sylvestris* and to determine the actual length of the primary (non-polyadenylated) transcript. A weak 3' UTR may generate read-through, which may affect the expression of the genes located in neighboring expression cassettes (Padidam and Cao, *BioTechniques* 31:328-334, 2001). Appropriate control of transcription termination can prevent read-through into sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved sequences to enable easy prediction of an effective 3' UTR.

From a practical standpoint, it may be beneficial that a 3' UTR used in a transgene cassette possesses certain characteristics. For example, a 3' UTR useful in accordance with the present invention may efficiently and effectively terminate transcription of the transgene and prevent read-through of the transcript into any neighboring DNA sequence, which can be comprised of another transgene cassette, as in the case of multiple cassettes residing in one T-DNA, or the neighboring chromosomal DNA into which the T-DNA has inserted. The 3' UTR optimally should not cause a reduction in the transcriptional activity imparted by the promoter, leader, and introns that are used to drive expression of the transgene. In plant biotechnology, the 3' UTR is often used for priming of amplification reactions of reverse-transcribed RNA extracted from the transformed plant and may be used to (1) assess the transcriptional activity or expression of the transgene cassette once integrated into the plant chromosome; (2) assess the copy number of insertions within the plant DNA; and (3) assess zygosity of the resulting seed after breeding. The 3' UTR may also be used in amplification reactions of DNA extracted from the transformed plant to characterize the intactness of the inserted cassette.

3' UTRs useful in providing expression of a transgene in plants may be identified based upon the expression of expressed sequence tags (ESTs) in cDNA libraries made from messenger RNA isolated from seed, flower, or any other tissues derived from, for example, Big bluestem (*Andropogon gerardii*), Plume Grass [*Saccharum ravennae* (*Erianthus ravennae*)], Green bristlegrass (*Setaria viridis*), Teosinte (*Zea mays* subsp. *mexicana*), Foxtail millet (*Setaria italica*), Coix (*Coix lacryma-jobi*) among others. Using methods known to those skilled in the art, libraries of cDNA may be made from tissues isolated from a plant species using flower tissue, seed, leaf, root, or other plant tissues. The resulting cDNAs are sequenced using various sequencing methods known in the art. The resulting ESTs are assembled into clusters using bioinformatics software such as clc_ref_assemble_complete version 2.01.37139 (CLC bio USA, Cambridge, Mass. 02142). Transcript abundance of each cluster is determined by counting the number of cDNA reads for each cluster. The identified 3' UTRs may be comprised of sequence derived from cDNA sequence, as well as sequence derived from genomic DNA. A cDNA sequence may be used to design primers, which may then be used with GenomeWalker™ (Clontech Laboratories, Inc, Mountain View, Calif.) libraries constructed following the manufacturer's protocol to clone the 3' region of the corresponding genomic DNA sequence to provide a longer termination sequence. Analysis of relative transcript abundance either by direct counts or normalized counts of observed sequence reads for each tissue library may be used to infer properties about patters of expression. For example, some 3' UTRs may be found in transcripts more abundant in root tissue rather than leaf tissue. This suggests that the transcript is highly expressed in root and that the properties of root expression may be attributable to the transcriptional regulation of the promoter, the leader, the introns, or the 3' UTR. Empirical testing of 3' UTRs identified by the properties of expression within specific organs, tissues, or cell types can result in the identification of 3' UTRs that enhance expression in those specific organs, tissues, or cell types.

Constructs and vectors may also include a transit peptide coding sequence that expresses a linked peptide that is useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.* 210:437-442, 1987) or the *Petunia hybrida* EPSPS CTP (CTP4) (see, della-Cioppa et al., *Proc. Natl. Acad. Sci. USA* 83:6873-6877, 1986) has been show to target heterologous EPSPS protein sequences to chloroplasts in transgenic plants (see, U.S. Pat. Nos. 5,627,061; 5,633,435; and 5,312,910; and EP 0218571; EP 189707; EP 508909; and EP 924299).

Transcribable Polynucleotide Molecules

As used herein, the term "transcribable polynucleotide molecule" refers to any DNA molecule capable of being transcribed into an RNA molecule, including, but not limited to, those having protein coding sequences and those producing RNA molecules having sequences useful for gene suppression. A "transgene" refers to a transcribable polynucleotide molecule heterologous to a host cell at least with respect to its location in the genome and/or a transcribable polynucleotide molecule artificially incorporated into a host cell's genome in the current or any prior generation of the cell.

A promoter of the present invention may be operably linked to a transcribable polynucleotide molecule that is heterologous with respect to the promoter molecule. As used herein, the term "heterologous" refers to the combination of two or more polynucleotide molecules when such a combination is not normally found in nature. For example, the two molecules may be derived from different species and/or the two molecules may be derived from different genes, e.g., different genes from the same species, or the same genes from different species. A promoter is thus heterologous with respect to an operably linked transcribable polynucleotide molecule if such a combination is not normally found in nature, i.e. that transcribable polynucleotide molecule is not naturally occurring operably linked in combination with that promoter molecule.

The transcribable polynucleotide molecule may generally be any DNA molecule for which expression of a RNA transcript is desired. Such expression of an RNA transcript may result in translation of the resulting mRNA molecule and thus protein expression. Alternatively, for example, a transcribable polynucleotide molecule may be designed to ultimately cause decreased expression of a specific gene or protein. In one embodiment, this may be accomplished by using a transcribable polynucleotide molecule that is oriented in the antisense direction. One of ordinary skill in the art is familiar with using such antisense technology. Briefly, as the antisense transcribable polynucleotide molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, in one embodiment of the present invention, a regulatory element may be operably linked to a transcribable polynucleotide molecule in order to modulate transcription of the transcribable polynucleotide molecule at a desired level or in a desired pattern when the construct is integrated in the genome of a plant cell. In one embodiment, the transcribable polynucleotide molecule comprises a protein-coding region of a gene, and the promoter affects the transcription of an RNA molecule that is translated and expressed as a protein product. In another embodiment, the transcribable polynucleotide molecule comprises an antisense region of a gene, and the promoter affects the transcription of an antisense RNA molecule, double-stranded RNA or other similar inhibitory RNA molecule in order to inhibit expression of a specific RNA molecule of interest in a target host cell.

Genes of Agronomic Interest

Transcribable polynucleotide molecules in accordance with the present invention may be genes of agronomic interest. As used herein, the term "gene of agronomic interest" refers to a transcribable polynucleotide molecule that, when expressed in a particular plant tissue, cell, or cell type, confers a desirable characteristic, such as one associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent, such as an antisense or RNAi molecule targeting a particular gene for suppression. The product of a gene of agronomic interest may act within the plant in order to cause an effect upon the plant physiology or metabolism, or may be act as a pesticidal agent in the diet of a pest that feeds on the plant.

In one embodiment of the present invention, a promoter is incorporated into a construct such that the promoter is operably linked to a transcribable polynucleotide molecule that is a gene of agronomic interest. The expression of the gene of agronomic interest is desirable in order to confer an agronomically beneficial trait. Without limitation, a beneficial agronomic trait may include, for example, herbicide tolerance, insect control, modified yield, fungal disease resistance, virus resistance, nematode resistance, bacterial disease resistance, plant growth and development, starch production, modified oil production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production, among others. Examples of genes of agronomic interest known in the art include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. USRE38,446; 6,716,474; 6,663,906; 6,476,295; 6,441,277; 6,423,828;

6,399,330; 6,372,211; 6,235,971; 6,222,098; and 5,716, 837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658; 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; and 6,476, 295), modified oil production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822, 141; 6,770,465; 6,706,950; 6,660,849; 6,596,538; 6,589, 767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. USRE37,543; 6,228,623; 5,958,745; and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristic or phenotype by encoding an RNA molecule that causes the targeted modulation of gene expression of an endogenous gene, for example via antisense (see for example, U.S. Pat. No. 5,107,065); inhibitory RNA ("RNAi," including modulation of gene expression via mechanisms mediated by miRNA, siRNA, trans-acting siRNA, and phased sRNA, e.g. as described in published applications US 2006/0200878 and US 2008/0066206, and in U.S. patent application Ser. No. 11/974,469); or cosuppression-mediated mechanisms. The RNA may also be a catalytic RNA molecule (e.g. a ribozyme or a riboswitch; see e.g. US 2006/0200878) engineered to cleave a desired endogenous mRNA product. Thus, any transcribable polynucleotide molecule that encodes a transcribed RNA molecule that affects an agronomically important phenotype or morphology change of interest may be useful for the practice of the present invention. Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829, and posttranscriptional gene suppression using a construct with a sense-oriented transcribable polynucleotide molecule to regulate gene expression in plants is disclosed in U.S. Pat. Nos. 5,283,184 and 5,231, 020. Expression of a transcribable polynucleotide in a plant cell can also be used to suppress plant pests feeding on the plant cell, for example, compositions isolated from coleopteran pests (U.S. Patent Publication No. US20070124836) and compositions isolated from nematode pests (U.S. Patent Publication No. US20070250947). Plant pests include, but are not limited to arthropod pests, nematode pests, and fungal or microbial pests. Exemplary transcribable polynucleotide molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule may include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding β-glucuronidase (GUS, described in U.S. Pat. No. 5,599,670), green fluorescent protein and variants thereof (GFP, described in U.S. Pat. Nos. 5,491,084 and 6,146,826), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4), are well known in the art. Herbicides for which transgenic plant tolerance has been demonstrated and to which the method of the present invention can be applied, may include, but are not limited to: amino-methyl-phosphonic acid, glyphosate, glufosinate, sulfonylureas, imidazolinones, bromoxynil, dalapon, dicamba, cyclohexanedione, protoporphyrinogen oxidase inhibitors, and isoxasflutole herbicides. Transcribable polynucleotide molecules encoding proteins involved in herbicide tolerance are known in the art, and may include, but are not limited to, a transcribable polynucleotide molecule encoding 5-enolpyruvylshikimate-3-phosphate synthase (EPSPS for glyphosate tolerance, described in U.S. Pat. Nos. 5,627,061; 5,633,435; 6,040, 497; and 5,094,945); a transcribable polynucleotide molecule encoding a glyphosate oxidoreductase and a glyphosate-N-acetyl transferase (GOX, described in U.S. Pat. No. 5,463,175; GAT, described in U.S. Patent Publication No. 20030083480; and dicamba monooxygenase, described in U.S. Patent Publication No. 20030135879); a transcribable polynucleotide molecule encoding bromoxynil nitrilase (Bxn for Bromoxynil tolerance, described in U.S. Pat. No. 4,810,648); a transcribable polynucleotide molecule encoding phytoene desaturase (crtI) described in Misawa, et al. (*Plant Journal* 4:833-840, 1993; and *Plant Journal* 6:481-489, 1994) for norflurazon tolerance; a transcribable polynucleotide molecule encoding acetohydroxyacid synthase (AHAS, aka ALS) described in Sathasiivan et al. (*Nucl. Acids Res.* 18:2188-2193, 1990) for tolerance to sulfonylurea herbicides; and the bar gene described in DeBlock, et al. (*EMBO Journal* 6:2513-2519, 1987) for glufosinate and bialaphos tolerance. The promoter molecules of the present invention may express linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Selectable secreted marker proteins fall into a number of classes, including small, diffusible proteins that are detectable, (e.g. by ELISA), small active enzymes that are detectable in extracellular solution (e.g, α-amylase, β-lactamase, phosphinothricin transferase), or proteins that are inserted or trapped in the cell wall (such as proteins that include a leader sequence such as that found in the expression unit of extension or tobacco pathogenesis related proteins, also known as tobacco PR-S). Other possible selectable marker genes will be apparent to those of skill in the art and are encompassed by the present invention.

Cell Transformation

The term "transformation" refers to the introduction of nucleic acid into a recipient host. As used herein, the term "host" refers to a bacterium, a fungus, or a plant, including any cells, tissue, organs, or progeny of the bacterium, fungus, or plant. For instance, a host cell according to the present invention may be any cell or organism, such as a plant cell, algal cell, algae, fungal cell, fungi, bacterial cell, insect cell, or the like. In an embodiment, hosts and transformed cells may include cells from: plants, *Aspergillus*, yeasts, insects, bacteria and algae. Plant tissues and cells of particular interest include, but are not limited to, protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacterium, fungus, or plant containing one or more heterologous polynucleic acid molecules.

There are many methods for introducing polynucleic acid molecules into plant cells. The method may generally comprise the steps of selecting a suitable host cell, transforming the host cell with a recombinant vector, and obtaining a transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.* 42: 205, 1991).

Technology for introduction of a DNA molecule into cells is well known to those of skill in the art. Methods and materials for transforming plant cells by introducing a plant DNA construct into a plant genome in the practice of this invention can include any of the well-known and demonstrated methods. Any transformation methods may be utilized to transform a host cell with one or more promoters and/or constructs of the present.

Regenerated transgenic plants can be self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, Principles of Plant Breeding, John Wiley & Sons, NY, U. of CA, Davis, Calif., 50-98, 1960; Simmonds, Principles of crop improvement, Longman, Inc., NY, 369-399, 1979; Sneep and Hendriksen, Plant breeding perspectives, Wageningen (ed), Center for Agricultural Publishing and Documentation, 1979; Fehr, Soybeans: Improvement, Production and Uses, 2nd Edition, Monograph, 16:249, 1987; Fehr, Principles of variety development, Theory and Technique, (Vol. 1) and Crop Species Soybean (Vol. 2), Iowa State Univ., Macmillan Pub. Co., NY, 360-376, 1987. Conversely, pollen from non-transgenic plants may be used to pollinate the regenerated transgenic plants.

The transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used to evaluate transgene expression.

The seeds of plants of this invention may be harvested from fertile transgenic plants and used to grow progeny generations of transformed plants of this invention, including hybrid plant lines comprising the construct of this invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleotide molecule to its progeny. Progeny includes any regenerable plant part or seed comprising the transgene derived from an ancestor plant. The transgenic plant is preferably homozygous for the transformed polynucleotide molecule and transmits that sequence to all offspring as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Mathematical Modeling

Figure 2A:
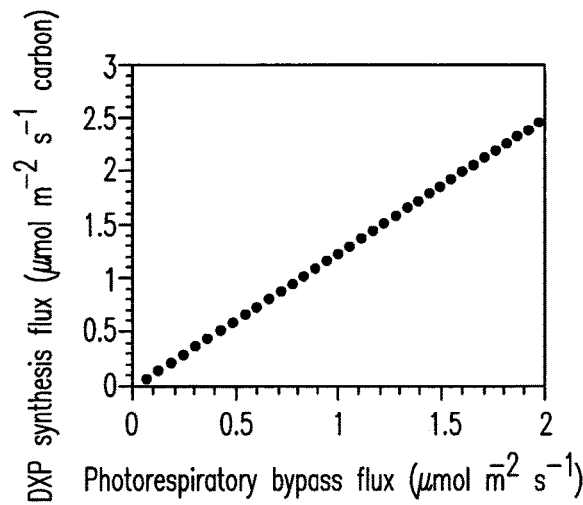
FIGS. 2A, 2B, and 2C —shows the modeling outcome of the pathway design shown in FIG. 1.
Figure 2B:
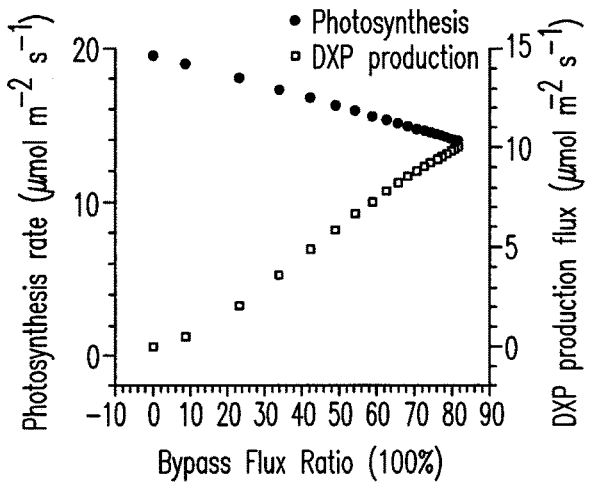
Figure 2C:
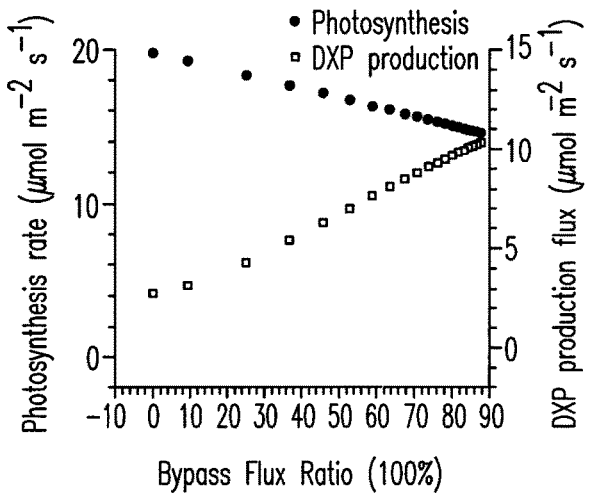

Mathematical modeling of pathway flux was carried out by combining all kinetics information of the enzymes. The new models were built based on the inventors' previous models on photosynthesis by integrating the terpene pathway (FIG. 1). The modeling outcome shows that the flux to terpene will respond to the bypass efficiency (FIG. 2A), and the increase of terpene yield will not collapse photosynthesis or will not decrease the photosynthesis with the same rate (FIG. 2B, C).

Example 2

Plant Materials

Seeds of high-squalene (G1) tobacco plants and tobacco plant transformants (pT1, pT2, pT3, and pT4 transformed G1) were sterilized with 70% (v/v) ethanol for 30 s, and then with 2% (v/v) sodium hypochlorite solution for 10 min, followed by rinsing 3 times in sterilized water. The basal medium for germination and initial growth of the seeds consisted of salts and vitamins of MS medium with appropriate antibiotics, solidified with 0.8% (w/v) agarose.

Example 3

Preparation of *Agrobacterium tumefaciens*

Four vector constructs (named pTERPENE1, 2, 3, 5; or pT1, 2, 3, and 5) (FIG. 3) were introduced into armed *Agrobacterium tumefaciens* strains GV3101 and COR308 via electroporation. A culture of *Agrobacterium rhizogenes* was initiated from glycerol stock and grown overnight at 28° C. with shaking (180 rpm) in liquid Luria-Bertani (LB) medium containing 50 mg 1-1 kanamycin, to mid-log phase (OD600=0.5). The *A. rhizogenes* cells were collected by centrifugation for 10 min at 4000 rpm and resuspended in liquid inoculation medium (MS salts and vitamins containing 30 g/L sucrose). The *Agrobacterium* cell density was adjusted to an OD600 of 1.0 for inoculation.

Example 4

Genetic Transformation of G1 Tobacco Line

The constructs described above and shown in FIG. 3 were transformed into transgenic tobacco line G1 overexpressing the farnesyl diphosphate synthase (FPS) and SQS genes. Excised leaves of 14-day-old high-squalene and limonene line tobacco plant seedlings were used as the explant material for co-cultivation with *A. tumefaciens* GV301 and COR308. The excised explants were dipped into the *A. tumefaciens* culture in liquid inoculation medium for 20 min, blotted dry on sterile filter paper, and incubated in the dark at 25° C. on agar-solidified MS medium with 2 mg/L of 2,4-Dichlorophenoxyacetic acid (2,4-D). After 2 days of co-cultivation, the explant tissues were washed in sterilized distilled water three times and transferred to MS medium containing salts, vitamins, 2 mg/L BAP, 30 g/L sucrose, 500 mg/L cefotaxime, 50 mg/L kanamycin, and 8 g/L plantagar. Putative plants were observed emerging from the wound sites after 3-4 weeks. Selected plants were transferred to rooting media (MS basal salts with 1 mg/L IAA. The rooted plants were transferred to culture vessels for further growth.

Example 5

Squalene Extraction and GC-MS Analysis

Figure 3:
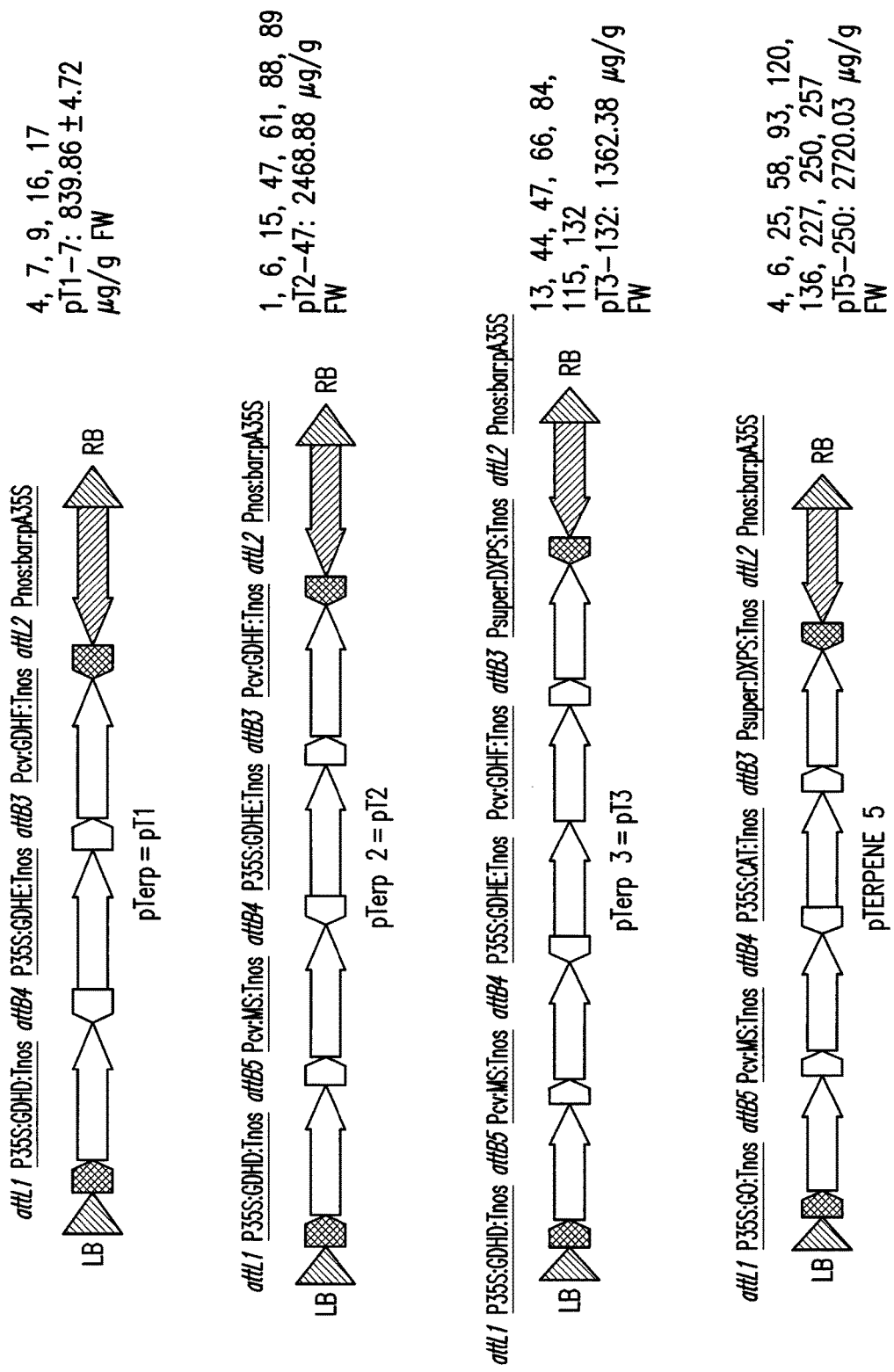
FIG. 3—shows the organization of the T-DNA region of different plant transformation vectors. The nptII gene provides kanamycin resistance; GDHD, GDHE, and GDHF encode the three subunits of bacterial glycolate dehydrogenase; MS encodes malate synthase; DXPS encodes 1-deoxy-D-xylulose-5-phosphate synthase; GCL encodes glyoxylate carboligase; TSR encodes tartronate semialdehyde reductase; GO encodes bacterial glycolate oxidase; CAT encodes catalase; DXR encodes 1-deoxy-D-xylulose-5-phosphate reductoisomerase. The vector further comprises suitable promoter, terminator, and transit peptide sequences. The right panel shows the representative terpene yield for transgenic tobacco containing the plant transformation vectors. Prior to the current study, the highest yield of terpene observed for stably transformed tobacco was 600 ug/g FW (formula weight), while the yield observed in the present invention is approximately two- to four-fold higher.
Figure 4:
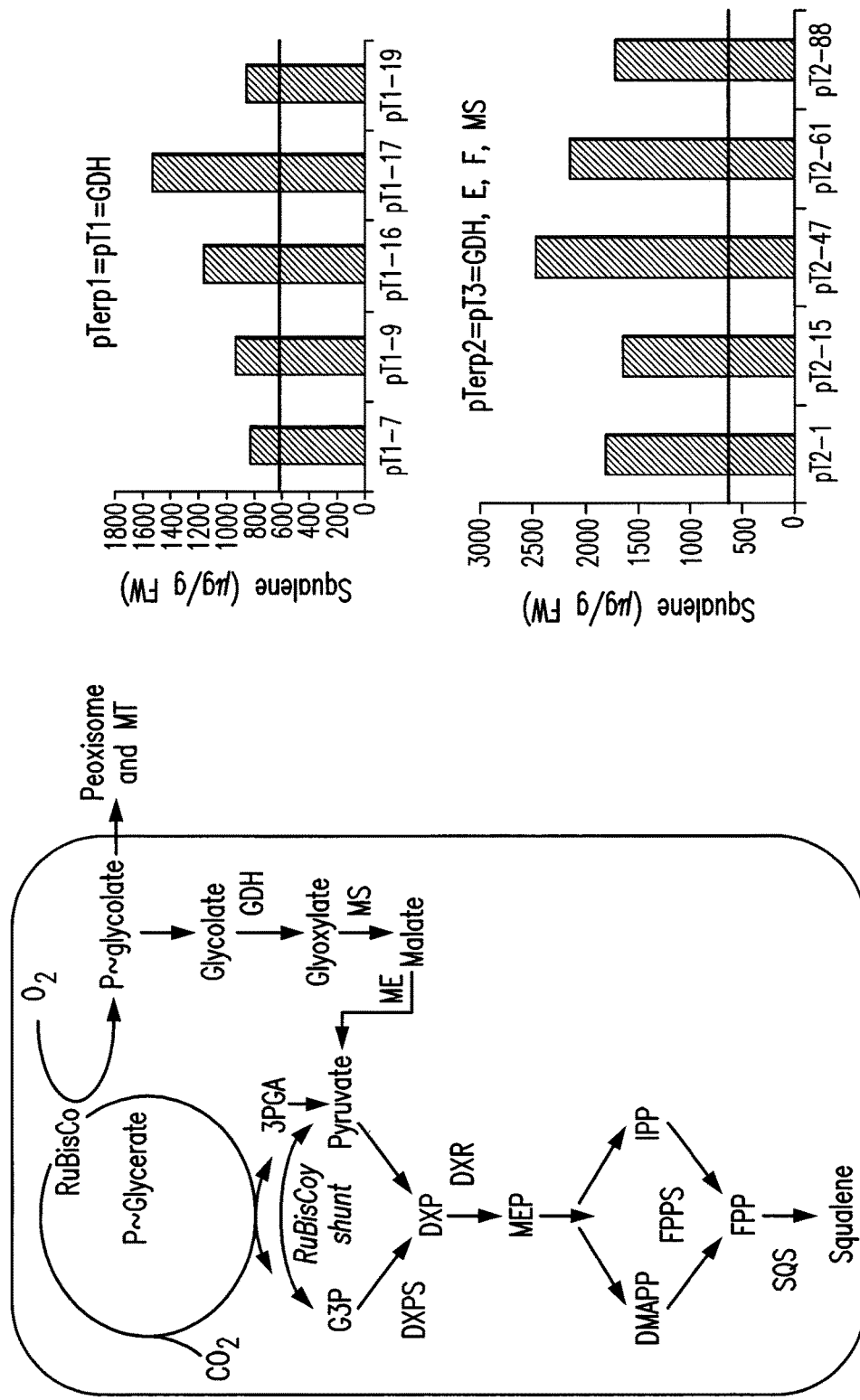
FIG. 4—shows the squalene levels of pT1 and pT2 plants. The left panel shows the pathway design. The right panels show squalene levels for selective transformants. The solid line in the plot is the current baseline level.
Figure 5:
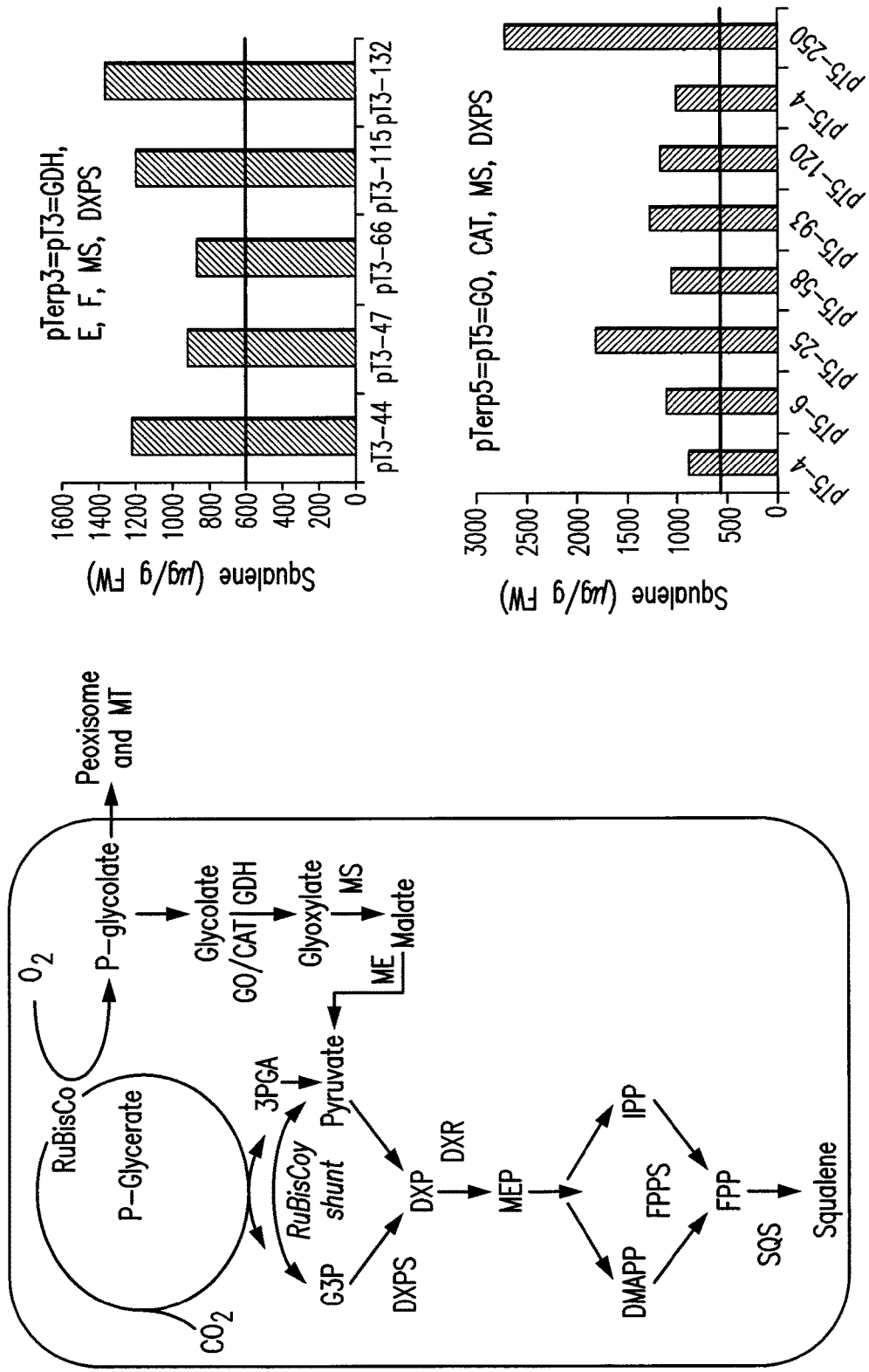
FIG. 5—shows squalene levels of pT3 and pT4 plants. The left panel shows the pathway design. The right panels show the squalene levels for selective transformants. The solid line in the plot is the current baseline level.

Five hundred positive transgenic leaves were collected with a 2-cm-diameter cork borer. Each sample was ground in liquid nitrogen, then extracted with 3 ml of hexane. The extracts were purified by passing through a 500-mg silica column with glasswool plugged glass pipette and 4 ml of additional hexane for the washing column. The eluate was analysis by GC-MS. Transgenic tobacco plants overexpressing pT1, 2, 3, and 5 accumulated over 2 to 5 times more squalene than that of the parental GI line. Thus, as shown in FIGS. 3-5, as well as Table 1, significant increase of terpene and other bioproduct is yielded by repartitioning carbon into additional sink.

Example 6

C14 Label Assay

Figure 6:
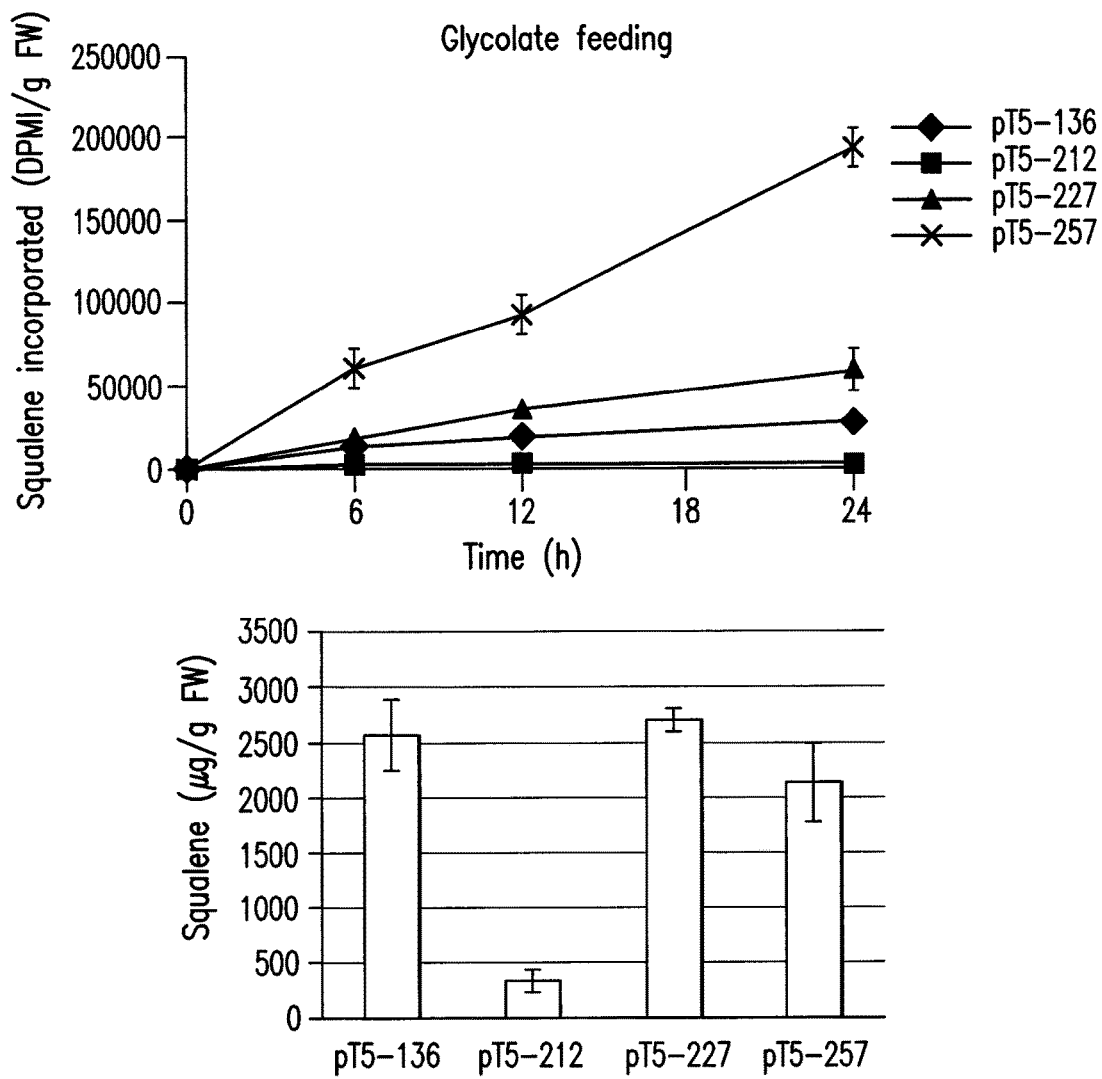
FIG. 6—shows the increase of C14-labeled glycolate rechanneling into terpene product in high squalene lines.

The C14-labeled glycolate was fed into plant leaves and the terpene product, particularly squalene, was extracted, and the C14 level was measured. As shown in FIG. 6, the level of squalene corresponded to the glycolate incorporation rate. The higher squalene levels corresponded to higher glycolate incorporation, indicating that glycolate redirection is important for squalene yield increase.

Example 7

Segregation Studies

The genetic segregation of the T1 transgenic plants was studied as shown in Table 1. The segregation study showed that some transgenic plants have near a 3:1 ratio with a single copy, while others do not. The high level of squalene was observed in all these transgenic lines, regardless of the gene copy numbers.

TABLE 1

Genetic segregation of T1 transgenic plants

| | Resistant | Susceptible | Ratio | T0 Squalene |
|---|---|---|---|---|
| pT1-4 | — | — | — | 670.56 |
| | 96 | 9 | 10.6:1 | |
| pT1-7 | 339 | 19 | 17.8:1 | 839.86 |
| | 211 | 17 | 12.4:1 | |
| pT1-9 | 196 | 10 | 19.6:1 | 940.10 |
| | 165 | 7 | 23.5:1 | |
| pT1-16 | 64 | 3 | 21.3:1 | 1160.34 |
| | 141 | 11 | 12.8:1 | |
| pT2-15 | 51 | 28 | 1.8:1 | 1659.47 |
| | 72 | 19 | 3.7:1 | |
| pT2-47 | 96 | 19 | 5.0:1 | 2468.88 |
| | 99 | 24 | 3.9:1 | |
| pT2-61 | 85 | 0 | 1.0:0 | 2148.75 |
| | 196 | 1 | 196:1 | |
| pT2-85 | 125 | 39 | 3.2:1 | 1776.61 |
| | 166 | 58 | 2.8:1 | |
| pT3-13 | 192 | 19 | 10.1:1 | 1362.38 |
| | 133 | 16 | 8.3:1 | |
| pT3-44 | 120 | 4 | 30.0:1 | 1224.33 |
| | 93 | 11 | 8.4:1 | |
| pT3-47 | 98 | 4 | 24.5:1 | 911.49 |
| | 117 | 9 | 13:1 | |
| pT3-66 | 62 | 5 | 12.4:1 | 863.24 |
| | 107 | 15 | 7.1:1 | |
| pT3-84 | 100 | 25 | 4.00:1 | 813.36 |
| | 118 | 34 | 3.4:1 | |
| pT3-115 | 57 | 3 | 19.0:1 | 1304.82 |
| | 39 | 2 | 19.5:1 | |
| pT5-4 | 92 | 30 | 3.0:1 | 872.39 |
| | 169 | 26 | 6.5:1 | |
| pT5-58 | — | — | — | 1060.72 |
| | 102 | 24 | 4.2:1 | |
| pT5-93 | 64 | 24 | 2.6:1 | 1276.37 |
| | 50 | 26 | 1.9:1 | |
| pT5-227 | — | — | — | 2713.93 |
| | 157 | 50 | 3.1:1 | |
| pT5-280 | 54 | 30 | 1.80:1 | 2720.03 |
| | 65 | 31 | 2.0:1 | |
| pT5-257 | 12 | 133 | 1:11.08 | 2142.70 |
| | 34 | 110 | 1:3.2 | |

What is claimed is:

1. A method of producing a terpene in a *Nicotiana* plant, said method comprising expressing in the *Nicotiana* plant a bacterial glycolate oxidase (GO) or a bacterial glycolate dehydrogenase (GDH), and a bacterial malate synthase (MS) gene of the glycolate catabolic cycle and a plant farnesyl diphosphate synthase (FPS) and squalene synthase (SQS) gene, wherein the glycolate oxidase (GO), glycolate dehydrogenase (GDH), malate synthase (MS), farnesyl diphosphate synthase (FPS) and squalene synthase (SQS) genes each include a chloroplast transit peptide coding sequence.

2. The method of claim 1, comprising further expressing in the *Nicotiana* plant a bacterial 1-deoxy-d-xylulose 5 phosphate synthase (DXPS) gene including a chloroplast transit peptide coding sequence.

3. The method of claim 1, wherein expression of said bacterial genes in the *Nicotiana* plant produces an elevated level of said terpene.

4. The method of claim 3, wherein the terpene is a monoterpene, sesquiterpene, diterpene, triterpene or tetraterpene.

5. The method of claim 4, wherein the terpene is a triterpene.

6. The method of claim 1, further comprising over-expression of said plant gene.

7. The method of claim 1, wherein said bacterial and plant genes are co-expressed.

8. A *Nicotiana* plant produced by the method of claim 1.

9. A part of the *Nicotiana* plant of claim 8, wherein said part comprises (i) a bacterial glycolate oxidase or a bacterial glycolate dehydrogenase, (ii) a bacterial malate synthase gene of the glycolate catabolic cycle, (iii) a plant farnesyl diphosphate synthase, and (iv) a squalene synthase gene, wherein the glycolate oxidase, glycolate dehydrogenase, malate synthase, farnesyl diphosphate synthase, and squalene synthase genes each include a chloroplast transit peptide coding sequence.

10. The method of claim 5, wherein the triterpene is squalene.

\* \* \* \* \*